(12) United States Patent
Bisaha

(10) Patent No.: US 10,070,647 B2
(45) Date of Patent: Sep. 11, 2018

(54) STABILIZED LOW-CONCENTRATION METSULFURON-METHYL LIQUID COMPOSITION

(71) Applicant: E. I. DU PONT DE NEMOURS AND COMPANY, Wilmington, DE (US)

(72) Inventor: John Joseph Bisaha, Hockessin, DE (US)

(*) Notice: Subject to any disclaimer, the term of this patent is extended or adjusted under 35 U.S.C. 154(b) by 0 days.

(21) Appl. No.: 15/038,935

(22) PCT Filed: Nov. 21, 2014

(86) PCT No.: PCT/US2014/066864
§ 371 (c)(1),
(2) Date: May 24, 2016

(87) PCT Pub. No.: WO2015/077587
PCT Pub. Date: May 28, 2015

(65) Prior Publication Data
US 2016/0374343 A1  Dec. 29, 2016

Related U.S. Application Data

(60) Provisional application No. 61/908,221, filed on Nov. 25, 2013, provisional application No. 62/036,935, filed on Aug. 13, 2014.

(51) Int. Cl.
*A01N 47/36* (2006.01)
*A01N 43/40* (2006.01)
*A01N 25/22* (2006.01)
*A01N 25/02* (2006.01)
*A01N 25/30* (2006.01)

(52) U.S. Cl.
CPC .......... *A01N 47/36* (2013.01); *A01N 25/02* (2013.01); *A01N 25/22* (2013.01); *A01N 25/30* (2013.01)

(58) Field of Classification Search
CPC combination set(s) only.
See application file for complete search history.

(56) References Cited

U.S. PATENT DOCUMENTS

| | | |
|---|---|---|
| 4,383,113 A | 5/1983 | Levitt |
| 4,481,029 A | 11/1984 | Levitt |
| 6,479,432 B1 | 11/2002 | Sixl |
| 2002/0016263 A1 | 2/2002 | Wurtz et al. |
| 2005/0026787 A1 | 2/2005 | Deckwer et al. |
| 2005/0113254 A1 | 5/2005 | Ziemer et al. |
| 2009/0131257 A1 | 5/2009 | Beestman et al. |
| 2010/0190648 A1* | 7/2010 | Tollington ............. A01N 25/04 504/234 |
| 2011/0021350 A1 | 1/2011 | Reap |

FOREIGN PATENT DOCUMENTS

| | | |
|---|---|---|
| AP | 112 A | 3/1990 |
| WO | 2007/027863 A2 | 3/2007 |
| WO | 2008/108973 A1 | 9/2008 |

OTHER PUBLICATIONS

Harmony M Safety Data Sheet, Du Pont, (2010).*
Bentone 34 brochure, Elementis Specialties, (2009).*

* cited by examiner

*Primary Examiner* — John D Pak
(74) *Attorney, Agent, or Firm* — Reed A Coats

(57) ABSTRACT

Disclosed are a single liquid-phase herbicide composition comprising by weight of the composition: (a) from 0.1 to 1% of metsulfuron-methyl; (b) from 1 to 20% of thifensulfuron-methyl; (c) from 30 to 93% of one or more fatty acid esters of $C_1$-$C_4$ alkanols; and (d) from 5 to 25% of one or more surfactants having an emulsifier property, and a process for preparing the composition.

13 Claims, No Drawings

STABILIZED LOW-CONCENTRATION METSULFURON-METHYL LIQUID COMPOSITION

FIELD OF THE INVENTION

This invention provides a stable liquid herbicide composition comprising metsulfuron-methyl not exceeding 1% of the composition by weight, which accommodates including higher concentrations of less active herbicides in the composition.

BACKGROUND OF THE INVENTION

Since its first marketing approval in 1984, metsulfuron-methyl has become one of the most commercially important herbicides for control of a wide range of grass and broad-leaved weeds in crops including wheat, barley, oats and triticale through post-emergence application (see *The Pesticide Manual*, Sixteenth Edition, C. MacBean ed., British Crop Protection Council, Hampshire, UK, 2012, pp. 782-3). Like other sulfonylurea herbicides, the mode of action of metsulfuron-methyl involves inhibition of the enzyme acetolactate synthase (ALS) found in plants but not animals, and therefore metsulfuron-methyl provides a valued combination of excellent efficacy against weeds with low use rates and very low toxicity to animals.

Since its introduction, metsulfuron-methyl has typically been formulated in herbicide products as solid compositions, such as granules, particularly water-dispersible or water-soluble granules, and tablets. Not only can granules and tablets be readily dispensed, but metsulfuron-methyl generally has excellent storage stability in solid compositions.

Although metsulfuron-methyl controls a wide range of weeds, combination with other active ingredients, particularly other herbicides, can be desirable to provide a broader spectrum of protection or for resistance management. Solid compositions are suitable for metsulfuron-methyl in combination with other high-melting active ingredients, but including active ingredients that are liquids or low-melting in a solid composition can be difficult.

Concentrated liquid compositions can readily include not only active ingredients that are liquids or low-melting but also high-melting active ingredients such as sulfonylurea herbicides, which generally are mostly present in the form of solid particles dispersed in a liquid carrier. Such liquid concentrate formulations can be easily measured and poured, and when diluted with water typically give easily sprayed aqueous solutions, emulsions or dispersions.

However, compared to solid formulations, liquid formulations of sulfonylureas are more prone to certain problems. When dissolved or dispersed in a liquid carrier, even a carrier comprising a nonaqueous solvent, sulfonylurea herbicides may be susceptible to decomposition. Also, crystal growth can occur during storage of concentrated liquid formulations in which active ingredients are dissolved or dispersed, and suspended active ingredients are prone to settling out, so that obtaining stable liquid formulations is challenging.

Because of its high herbicidal activity, metsulfuron-methyl is typically applied at very low rates, e.g., 4-8 g/ha. Accordingly when combined with much higher use rate herbicides in a concentrated formulated composition, metsulfuron-methyl must be in low concentration to accommodate a sufficiently high concentration of higher use rate herbicides in the composition. However, it has now been found that although metsulfuron-methyl is sufficiently stable at high concentration in liquid carriers comprising one or more fatty acid esters of $C_1$-$C_4$ alkanols in the presence of one or more surfactants having an emulsifier property, at concentrations of 1% or less, metsulfuron-methyl is susceptible to undergoing decomposition to a commercially undesirable extent during storage of the composition.

Remarkably, as described herein, a surprising means of stabilization of low concentrations of metsulfuron-methyl in such a liquid composition has now been discovered, thus providing a new stabilized liquid composition for dilution with water and application to undesirable vegetation to be controlled.

SUMMARY OF THE INVENTION

This invention is directed to a single liquid-phase herbicide composition comprising by weight of the composition:
(a) from 0.1 to 1% of metsulfuron-methyl;
(b) from 1 to 20% of thifensulfuron-methyl;
(c) from 30 to 93% of one or more fatty acid esters of $C_1$-$C_4$ alkanols; and
(d) from 5 to 25% of one or more surfactants having an emulsifier property.

This invention also relates to a process for preparing said composition, the process comprising milling components (a) and (b) together in a liquid carrier comprising components (c) and (d).

DETAILED DESCRIPTION OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, or method that comprises a list of elements is not necessarily limited to only those elements but may include other elements not expressly listed or inherent to such composition, mixture, process, or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following:

A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "single liquid-phase composition" and derivative terms such as "single liquid-phase herbicide composition" refer to compositions consisting of a single liquid phase. The term "single liquid-phase composition" therefore excludes compositions comprising a plurality of liquid phases such as emulsions. The term "single liquid-phase composition" does not exclude compositions comprising one or more solid phases in addition to the single liquid phase, such as suspensions and dispersions of solid particles.

As used in the present disclosure and claims, the term "fatty acid" refers to a monocarboxylic acid having a hydrocarbon chain containing 3 to 23, more particularly 3 to 21 carbon atoms. The hydrocarbon chain may be branched and may be unsaturated (e.g., contain one or more carbon-carbon double bonds).

As used in the present disclosure and claims, the term "polymerized fatty acid" generally refers to a polymer derived from fatty acid monomers. Polymerized fatty acids include, for example, polymers formed by esterification of the carboxylic acid and hydroxy functions of hydroxy fatty acids such as ricinoleic acid or hydrogenated ricinoleic acid (12-hydroxyoctadecanoic acid). Polymerized fatty acids include both homopolymers, formed, for example, from just one fatty acid monomer, e.g., 12-hydroxyoctadecanoic acid, and copolymers formed from two or more fatty acid monomers, e.g., both ricinoleic acid and 12-hydroxyoctadecanoic acid. Furthermore the term "polymerized fatty acid" also includes fatty acid polymers having fatty acid units terminating polymerization, for example a non-hydroxy fatty acid in a polymer of hydroxy fatty acids (e.g., 12-hydroxyoctadecanoic acid homopolymer, octadecanoate). These can be considered fatty acid esters of fatty acid polymers.

Particle size (or size of particles) as referred to herein relates to the volume moment mean, also known as the volume mean and the De Broucker mean. The principles of particle size analysis are well known to those skilled in the art; for a technical paper providing a summary, see A. Rawle, "Basic Principles of Particle Size Analysis" (document MRK034 published by Malvern Instruments Ltd., Malvern, Worcestershire, UK). Volume distributions of particles in liquid suspensions can be conveniently measured by such techniques as Low Angle Laser Light Scattering (also known as LALLS and Laser Diffraction), which relies on the fact that diffraction angle is inversely proportional to particle size. Commercially available instruments suitable for analyzing using LALLS the volume distributions of particles in liquid suspensions include the Mastersizer 2000 (Malvern Instruments, Worcestershire, UK). The Mastersizer can determine D10, D50 and D90 percentiles, which are size values corresponding to the cumulative distribution at 10%, 50% and 90%. Thus, the D10 value represents a size value below which 10% of the cumulative distribution is present, and similarly D90 represents a size value below which 90% of the cumulative distribution occurs. The D50 value therefore, corresponds to the median diameter and divides the distribution exactly in half.

Embodiments of the present invention as described in the Summary of the Invention include those described below.

Embodiment A1

The composition according to the Summary of the Invention wherein component (a) is at least 0.2% of the composition by weight.

Embodiment A2

The composition of Embodiment A1 wherein component (a) is at least 0.3% of the composition by weight.

Embodiment A3

The composition of Embodiment A2 wherein component (a) is at least 0.4% of the composition by weight.

Embodiment A4

The composition according to the Summary of the Invention or any one of Embodiments A1 through A3 wherein component (a) is not more than 0.9% of the composition by weight.

Embodiment A5

The composition of Embodiment A4 wherein component (a) is not more than 0.8% of the composition by weight.

Embodiment A6

The composition of Embodiment A5 wherein component (a) is not more than 0.7% of the composition by weight.

Embodiment A7

The composition of Embodiment A6 wherein component (a) is not more than 0.6% of the composition by weight.

Embodiment B1

The composition according to the Summary of the Invention or any one of Embodiments A1 through A7 wherein component (b) is at least 2% of the composition by weight.

Embodiment B2

The composition according to the Summary of the Invention or any one of Embodiments A1 through B1 wherein component (b) is not more than 10% of the composition by weight.

Embodiment B3

The composition of Embodiment B2 wherein component (b) is not more than 8% of the composition by weight.

Embodiment B4

The composition of Embodiment B3 wherein component (b) is not more than 6% of the composition by weight.

Embodiment B5

The composition of Embodiment B4 wherein component (b) is not more than 5% of the composition by weight.

Embodiment B6

The composition of Embodiment B5 wherein component (b) is not more than 4% of the composition by weight.

Embodiment C1

The composition according to the Summary of the Invention or any one of Embodiments A1 through B6 wherein component (c) is at least 35% of the composition by weight.

Embodiment C2

The composition of Embodiment C1 wherein component (c) is at least 40% of the composition by weight.

Embodiment C3

The composition according to the Summary of the Invention or any one of Embodiments A1 through C2 wherein component (c) is not more than 90% of the composition by weight.

Embodiment C4

The composition of Embodiment C3 wherein component (c) is not more than 80% of the composition by weight.

Embodiment C5

The composition of Embodiment C4 wherein component (c) is not more than 65% of the composition by weight.

Embodiment C6

The composition of Embodiment C5 wherein component (c) is not more than 60% of the composition by weight.

Embodiment C7

The composition of Embodiment C6 wherein component (c) is not more than 55% of the composition by weight.

Embodiment C8

The composition according to the Summary of the Invention or any one of Embodiments A1 through C7 wherein component (c) comprises one or more $C_1$-$C_4$ alkyl esters of fatty acids containing 8 to 22 carbon atoms.

Embodiment C9

The composition of Embodiment C8 wherein at least 80% by weight of component (c) consists of esters of fatty acids containing 8 to 22 carbon atoms.

Embodiment C10

The composition of Embodiment C9 wherein at least 90% by weight of component (c) consists of esters of fatty acids containing 8 to 22 carbon atoms.

Embodiment C11

The composition according to the Summary of the Invention or any one of Embodiments A1 through C10 wherein component (c) comprises methyl esters of one or more fatty acids.

Embodiment C12

The composition according to the Summary of the Invention or any one of Embodiments A1 through C11 wherein component (c) comprises one or more methylated vegetable (e.g., seed) oils.

Embodiment C13

The composition of Embodiment C12 wherein component (c) comprises one or more methylated seed oils of sunflower, soybean, rapeseed, cotton, linseed, oil palm or coconut.

Embodiment C14

The composition of Embodiment C13 wherein component (c) comprises one or more methylated seed oils of soybean, rapeseed or coconut.

Embodiment C15

The composition of Embodiment C14 wherein component (c) comprises methylated soybean oil.

Embodiment C16

The composition of Embodiment C14 wherein component (c) comprises methylated coconut oil.

Embodiment C17

The composition of Embodiment C14 wherein component (c) comprises a mixture of methylated soybean oil and methylated coconut oil.

Embodiment C18

The composition according to the Summary of the Invention or any one of Embodiments A1 through C17 wherein component (c) in its isolated form (i.e. not part of the composition) has a cloud point (according to ASTM Standard Method D2500 (1994)) less than 15° C.

Embodiment C19

The composition according to the Summary of the Invention or any one of Embodiments A1 through C18 at a temperature of at least 15° C.

Embodiment C20

The composition according to the Summary of the Invention or any one of Embodiments A1 through C19 having a liquid carrier formed by (i.e. comprising) component (c).

Embodiment D1

The composition according to the Summary of the Invention or any one of Embodiments A1 through C20 wherein component (d) is at least 10% of the composition by weight.

Embodiment D2

The composition according to the Summary of the Invention or any one of Embodiments A1 through D1 wherein component (d) is not more than 20% of the composition by weight.

Embodiment D3

The composition according to the Summary of the Invention or any one of Embodiments A1 through D2 wherein component (d) comprises at least one surfactant selected from alkylbenzenesulfonates, alkylnaphthalenesulfonates, ethoxylated triglycerides, ethoxylated tri-styryl phenols, ethoxylated aliphatic alcohols, ethoxylated sorbitan mono- and tri-esters, ethoxylated sorbitol hexa-esters and polyoxyethylene-polyoxypropylene block copolymers, including mixtures thereof.

Embodiment D4

The composition according to the Summary of the Invention or any one of Embodiments A1 through D3 wherein component (d) comprises at least one surfactant selected from anionic surfactants and at least one surfactant selected from nonionic surfactants.

Embodiment D5

The composition according to the Summary of the Invention or any one of Embodiments A1 through D4 wherein component (d) is dissolved in component (c) forming the liquid carrier of the composition.

Embodiment E1

The composition according to the Summary of the Invention or any one of Embodiments A1 through D5 further comprising (e) up to 40% of one or more biologically active agents other than metsulfuron-methyl and thifensulfuron-methyl.

Embodiment E2

The composition of Embodiment E1 wherein component (e) is at least 0.1% of the composition by weight.

Embodiment E3

The composition of Embodiment E2 wherein component (e) is at least 1% of the composition by weight.

Embodiment E4

The composition of Embodiment E3 wherein component (e) is at least 5% of the composition by weight.

Embodiment E5

The composition of Embodiment E4 wherein component (e) is at least 10% of the composition by weight.

Embodiment E6

The composition of Embodiment E5 wherein component (e) is at least 15% of the composition by weight.

Embodiment E7

The composition of Embodiment E6 wherein component (e) is at least 20% of the composition by weight.

Embodiment E8

The composition according to the Summary of the Invention or any one of Embodiments A1 through E7 wherein component (e) is not more than 35% of the composition by weight.

Embodiment E9

The composition of Embodiment E8 wherein component (e) is not more than 30% of the composition by weight.

Embodiment E10

The composition according to the Summary of the Invention or any one of Embodiments A1 through E9 wherein component (e) comprises one or more herbicides or herbicide safeners.

Embodiment E11

The composition according to the Summary of the Invention or any one of Embodiments A1 through E10 wherein component (e) comprises one or more herbicides.

Embodiment E12

The composition according to the Summary of the Invention or any one of Embodiments A1 through E11 wherein component (e) comprises one or more fluroxypyr esters.

Embodiment E13

The composition according to the Summary of the Invention or any one of Embodiments A1 through E12 wherein the composition comprises at least 5% by weight of one or more fluroxypyr esters.

Embodiment E14

The composition of Embodiment E13 wherein the composition comprises at least 15% by weight of one or more fluroxypyr esters.

Embodiment E15

The composition according to the Summary of the Invention or any one of Embodiments A1 through E14 wherein the composition comprises not more than 40% by weight of one or more fluroxypyr esters.

Embodiment E16

The composition of Embodiment E15 wherein the composition comprises not more than 25% by weight of one of more fluroxypyr esters.

Embodiment E17

The composition according to the Summary of the Invention or any one of Embodiments A1 through E11 wherein component (e) comprises one or more bromoxynil esters.

Embodiment E18

The composition of Embodiment E17 wherein component (d) comprises one or more $C_6$-$C_{10}$ alkanoate esters of bromoxynil.

Embodiment E19

The composition according to the Summary of the Invention or any one of Embodiments A1 through E18 wherein the composition comprises at least 5% by weight of one or more bromoxynil esters.

Embodiment E20

The composition of Embodiment E19 wherein the composition comprises at least 25% by weight of one or more bromoxynil esters.

Embodiment E21

The composition according to the Summary of the Invention or any one of Embodiments A1 through E20 wherein the composition comprises not more than 40% by weight of one or more bromoxynil esters.

Embodiment E22

The composition of Embodiment E21 wherein the composition comprises not more than 35% by weight of one or more bromoxynil esters.

Embodiment E23

The composition according to the Summary of the Invention or any one of Embodiments A1 through E22 wherein component (e) is dissolved in component (c) forming the liquid carrier of the composition.

Embodiment F1

The composition according to the Summary of the Invention or any one of Embodiments A1 through E23 further comprising (f) up to 63% of one or more additional formulating ingredients.

Embodiment F2

The composition of Embodiment F1 wherein component (f) is at least 0.1% of the composition by weight.

Embodiment F3

The composition of Embodiment F2 wherein component (f) is at least 1% of the composition by weight.

Embodiment F4

The composition of Embodiment F3 wherein component (f) is at least 2% of the composition by weight.

Embodiment F5

The composition of Embodiment F4 wherein component (f) is at least 3% of the composition by weight.

Embodiment F6

The composition of any one of Embodiments F1 through F5 wherein component (f) is not more than 60% of the composition by weight.

Embodiment F7

The composition of Embodiment F6 wherein component (f) is not more than 50% of the composition by weight.

Embodiment F8

The composition of Embodiment F7 wherein component (f) is not more than 40% of the composition by weight.

Embodiment F9

The composition of Embodiment F8 wherein component (f) is not more than 30% of the composition by weight.

Embodiment F10

The composition of Embodiment F9 wherein component (f) is not more than 20% of the composition by weight.

Embodiment F11

The composition of Embodiment F10 wherein component (f) is not more than 15% of the composition by weight.

Embodiment F12

The composition of Embodiment F11 wherein component (f) is not more than 10% of the composition by weight.

Embodiment F13

The composition of any one of Embodiments F1 through F12 wherein component (f) comprises at least one constituent selected from (1) surfactants not having a significant emulsifier property, and (2) thickening agents.

Embodiment F14

The composition according to the Summary of the Invention or any one of Embodiments A1 through F13 wherein the composition comprises (i.e. as a constituent in component (f)) one or more surfactants having a dispersant property but not (having) an emulsifier property.

Embodiment F15

The composition of Embodiment F14 wherein the composition comprises by weight up to 10% of the surfactant constituent (i.e. one or more surfactants) having a dispersant property but not an emulsifier property.

Embodiment F16

The composition of Embodiment F15 wherein the composition comprises by weight up to 5% of the surfactant constituent (i.e., one or more surfactants) having a dispersant property but not an emulsifier property.

Embodiment F17

The composition of any one of Embodiments F14 through F16 wherein the composition comprises by weight at least 0.1% of the surfactant constituent having a dispersant property but not an emulsifier property.

Embodiment F18

The composition of Embodiment F17 wherein the composition comprises by weight at least 1% of the surfactant constituent having a dispersant property but not an emulsifier property.

Embodiment F19

The composition of Embodiment F18 wherein the composition comprises by weight at least 2% of the surfactant constituent having a dispersant property but not an emulsifier property.

Embodiment F20

The composition of any one of Embodiments F14 through F19 wherein the surfactant constituent having a dispersant property but not an emulsifier property comprises one or more polymerized fatty acids.

Embodiment F21

The composition of Embodiment F20 wherein the surfactant constituent having a dispersant property but not an emulsifier property comprises 12-hydroxyoctadecanoic acid homopolymer (CAS Number 27924-99-8), ricinoleic acid homopolymer (CAS Number 27925-02-6), or a fatty acid ester thereof.

Embodiment F22

The composition of Embodiment F21 wherein the surfactant constituent having a dispersant property but not an emulsifier property comprises 12-hydroxyoctadecanoic acid homopolymer, octadecanoate (CAS Number 58128-22-6).

Embodiment F23

The composition according to the Summary of the Invention or any one of Embodiments A1 through F22 wherein the composition or the surfactant constituent having a dispersant property but not an emulsifier property comprises one or more polymerized fatty acids in an amount of 2 to 5% of the composition by weight.

Embodiment F24

The composition according to the Summary of the Invention or any one of Embodiments A1 through F23 wherein the composition comprises (i.e. as a constituent in component (f)) one or more thickening agents.

Embodiment F25

The composition of Embodiment F24 wherein the composition comprises by weight up to 5% of the thickening agent constituent (i.e. one or more thickening agents).

Embodiment F26

The composition of Embodiment F25 wherein the composition comprises by weight not more than 4% of the thickening agent constituent.

Embodiment F27

The composition of Embodiment F26 wherein the composition comprises by weight not more than 3% of the thickening agent constituent.

Embodiment F28

The composition of Embodiment F27 wherein the composition comprises by weight not more than 2% of the thickening agent constituent.

Embodiment F29

The composition of any one of Embodiments F24 through F28 wherein the composition comprises by weight at least 0.1% of the thickening agent constituent.

Embodiment F30

The composition of Embodiment F29 wherein the composition comprises by weight at least 0.5% of the thickening agent constituent.

Embodiment F31

The composition of any one of Embodiments F24 through F30 wherein the thickening agent constituent comprises one or more silicas or silicates.

Embodiment F32

The composition of Embodiment F31 wherein the thickening agent constituent comprises one or more organically modified silicas or silicates.

Embodiment F33

The composition of any one of Embodiments F24 through F32 wherein the thickening agent constituent comprises one or more organically modified clays.

Embodiment F34

The composition according to the Summary of the Invention or any one of Embodiments A1 through F33 comprising by weight from 0.5 to 5% of one or more organically modified clays.

Embodiment G1

The composition according to the Summary of the Invention or any one of Embodiments A1 through F34 not containing more than 10% water by weight.

Embodiment G2

The composition according to Embodiment G1 not containing more than 5% water by weight.

Embodiment G3

The composition according to Embodiment G2 not containing more than 3% water by weight.

Embodiment G4

The composition according to Embodiment G3 not containing more than 2% water by weight.

Embodiment G5

The composition according to Embodiment G4 not containing more than 1% water by weight.

Embodiments of this invention, including Embodiments A1 through G5 above as well as any other embodiments described herein, can be combined in any manner. In addition, embodiments of this invention, including Embodiments A1 through G5 above as well as any other embodiments described herein, and any combination thereof, pertain to not only the composition but also to processes for preparation of the composition and intermediate mixtures and compositions.

As described in the Summary of the Invention, this invention is directed to a single liquid-phase herbicide composition comprising by weight of the composition (a) from 0.1 to 1% of metsulfuron-methyl; (b) from 1 to 20% of thifensulfuron-methyl; (c) from 30 to 93% of one or more fatty acid esters of $C_1$-$C_4$ alkanols; and (d) from 5 to 25% of one or more surfactants having an emulsifier property (i.e. an emulsifier). The liquid carrier of this composition comprises component (c) and provides a continuous liquid medium in which other components are dissolved or dispersed. As will be described further, components (a) and (b), both of which are herbicidal, are mostly suspended as solid particles in the present composition, and accordingly the composition can be regarded as a herbicidal oil dispersion formulation, i.e. a suspension of solid particles of components (a) and (b) dispersed in oily component (c).

The present composition contains as component (a) the chemical compound methyl 2-[[[[(4-methoxy-6-methyl-1,3,5-triazin-2-yl)amino]carbonyl]amino]sulfonyl]benzoate, which has the common name metsulfuron-methyl and the molecular structure shown as Formula 1.

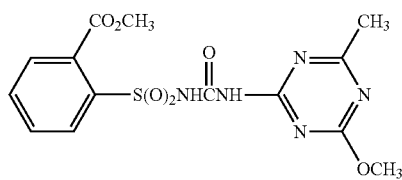

Methods for preparation of metsulfuron-methyl are disclosed in U.S. Pat. No. 4,383,113, and this herbicidal active ingredient is further described in *The Pesticide Manual*, Sixteenth Edition, C. MacBean ed., British Crop Protection Council, Hampshire, UK, 2012, pp. 782-783), which discloses a melting point of 162° C. Metsulfuron-methyl has relatively low solubility in solvents of low polarity such as fatty acid esters of $C_1$-$C_4$ alkanols, and thus is present mostly as solid particles in the present composition. Of note is at least 90%, 95%, 98% or 99% of the metsulfuron-methyl being in the form of suspended solid rather than dissolved. In the present composition, the metsulfuron-methyl of component (a) is typically in the free acid form having the molecular structure depicted as Formula 1, rather than as a salt (e.g., wherein the sulfonylurea bridge —S(O)$_2$NHC(=O)N— is deprotonated).

In the present composition, metsulfuron-methyl is included in an amount of 0.1 to 1% by weight. More typically, the amount of metsulfuron-methyl is at least 0.2%, or 0.3% or 0.4%, and not more than 0.9%, or 0.8%, or 0.7% or 0.6% of the composition by weight. This low concentration of metsulfuron-methyl accommodates the inclusion of not only the other required components and other formulating auxiliaries, but also greater concentrations of other optional active ingredients, including herbicides that are typically applied at application rates much greater than metsulfuron-methyl. It is also at this low concentration that, in the absence of a stabilizer, metsulfuron-methyl is found to be insufficiently stable on storage on contact with the liquid medium comprising a fatty acid ester of a $C_1$-$C_4$ alkanol in the presence of a surfactant having an emulsifier property.

In this regard, the present composition contains as component (b) the chemical compound methyl 3-[[[[(4-methoxy-6-methyl-1,3,5-triazin-2-yl)amino]carbonyl]amino]-sulfonyl]-2-thiophenecarboxylate, which has the common name thifensulfuron-methyl and the molecular structure shown as Formula 2.

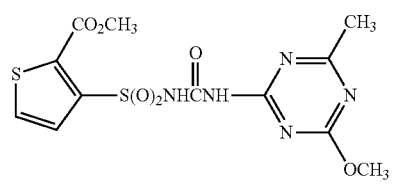

Methods for preparation of thifensulfuron-methyl are disclosed in U.S. Pat. No. 4,481,029, and this herbicidal active ingredient is further described in *The Pesticide Manual*, Sixteenth Edition, C. MacBean ed., British Crop Protection Council, Hampshire, UK, 2012, pp. 1109-1110), which discloses a melting point of 176° C. Thifensulfuron-methyl has relatively low solubility in solvents of low polarity such as fatty acid esters of $C_1$-$C_4$ alkanols, and thus is present mostly as solid particles in the present composition. Of note is at least 90%, 95%, 98% or 99% of the thifensulfuron-methyl being in the form of suspended solid rather than dissolved. In the present composition, the thifensulfuron-methyl of component (b) is typically in the free acid form having the molecular structure depicted as Formula 2, rather than as a salt (e.g., wherein the sulfonylurea bridge —S(O)$_2$NHC(=O)N— is deprotonated).

In the present composition, thifensulfuron-methyl is included as component (b) in an amount of 1 to 20% by weight. More typically, the amount of thifensulfuron-methyl is at least 2%, and not more than 10%, or 8%, or 6%, or 5%, or 4% of the composition by weight. Surprisingly, this concentration of thifensulfuron-methyl in component (b) has now been discovered to remarkably enhance the stability the metsulfuron-methyl of component (a) in the present composition, while at the same time the thifensulfuron-methyl shows minimal degradation.

Although herbicidal, thifensulfuron-methyl like metsulfuron-methyl is relatively safe to wheat, barley, oats and triticale crops. Therefore including the concentrations specified for thifensulfuron-methyl in combination with metsulfuron-methyl in the present composition retains the utility of the composition for selective control of undesired vegetation in wheat, barley, oats and triticale crops. Also, because thifensulfuron-methyl generally degrades more rapidly than metsulfuron-methyl in the environment, including thifensulfuron-methyl in the present composition does not restrict the rotational crop attributes of the present composition. Furthermore, because thifensulfuron-methyl is herbicidal, its inclusion in the composition may provide an improved spectrum or other benefits for weed control.

The present composition contains as component (c) one or more fatty acid esters of $C_1$-$C_4$ alkanols in the amount of 30 to 93% of the composition by weight. More typically, the amount of component (c) is at least 35% or 40%, and not more than 90%, 80%, 65%, 60% or 55% of the composition by weight.

Fatty acid esters of $C_1$-$C_4$ alkanols are simple esters between the carboxylic acid functionality of fatty acids and hydroxylic functionality of $C_1$-$C_4$ alkanols. Fatty acid esters of $C_1$-$C_4$ alkanols are not fatty acid esters of glycerol and thus are not properly regarded as vegetable oils. Instead, as described further below, fatty acid esters of $C_1$-$C_4$ alkanols can be synthesized by chemical transformation methods from vegetable oils and $C_1$-$C_4$ alkanols.

The $C_1$-$C_4$ alkanol-derived portions of the fatty acid esters can be unbranched (i.e. straight-chain) or branched, but are typically unbranched. For reasons including favorable physical properties, commercial availability and cost, preferably the fatty acid esters are fatty acids esterified with $C_1$-$C_2$ alkanols and more preferably $C_1$ alkanol (i.e. methanol). The fatty acid alkanol esters in a composition of the present invention can be derived from a mixture of alcohols (e.g., methanol and ethanol).

The fatty acid portions of the fatty acid esters of alkanols consist of a carbonyl moiety bound to a hydrocarbon chain, which can be unbranched or branched, but is typically unbranched in natural sources. The hydrocarbon chain can be saturated or unsaturated; typically the hydrocarbon chain is saturated (i.e. alkyl) or contains 1 or 2 (occasionally more) carbon-carbon double bonds (i.e. alkenyl). Fatty acid esters of alkanols formed from fatty acids containing an odd number of carbon atoms (i.e. even number of carbon atoms in the hydrocarbon chain) are useful in the compositions of the present invention as well as fatty acid esters of alkanols formed from fatty acids containing an even number of carbon atoms (i.e. odd number of carbon atoms in the hydrocarbon chain). However, fatty acids obtained from natural sources typically contain an even number of carbon atoms, and therefore esters of fatty acids containing an even number of carbon atoms are preferred for reason of commercial availability and cost.

As already mentioned, fatty acids contain at least 4 carbon atoms and are limited to about 22 (rarely 24) carbon atoms from natural sources. Although alkanol esters of lower fatty acids (e.g., containing as few as 4 carbon atoms) are useful for the present compositions, alkanol esters of fatty acids having at least 8, more preferably at least 10, carbon atoms are preferred because of favorable physical properties (e.g., low volatility). Alkanol esters of lower fatty acids can be mixed with alkanol esters of higher fatty acids to decrease polarity, water solubility and volatility. As fatty acids obtained from natural sources typically contain 8 to 22 carbon atoms, more typically 10 to 22 carbon atoms, alkanol esters of these fatty acids are preferred for reason of commercial availability and cost.

As already mentioned, fatty acid compositions obtained from natural sources (e.g., seed oils) typically consist of fatty acids having a range of chain lengths and different degrees of unsaturation. Alkanol fatty acid ester compositions (i.e. compositions comprising fatty acid esters of alkanols) derived from such fatty acid mixtures can be useful in the compositions of the present invention without need to first separate the fatty acid esters. For reason of cost, not separating the fatty acid esters is preferred. Also, the presence of a range of chain lengths and unsaturation instead of a single, saturated chain length facilitates maintaining, at typical storage and use temperatures of at least 15° C., component (c) in pure form as a clear liquid and in the composition as a liquid not containing alkanol fatty acid ester solids. Therefore preferred is the present composition wherein component (c) in its isolated form (i.e. not part of the composition) has a cloud point (according to ASTM Standard Method D2500 (1994)) less than 15° C. Cloud point is the temperature at which small crystals form in a liquid. Also preferred is the composition at a temperature of at least 15° C., which will ensure the absence of alkanol fatty acid ester solids if component (c) has a cloud point of less than 15° C.

Suitable alkanol fatty acid ester compositions obtained from plant-derived starting materials include seed and fruit oils of sunflower, rapeseed, olive, corn, soybean, cotton, oil palm, coconut and linseed. Of note is a composition of the invention wherein the one or more fatty acid esters of alkanols (i.e. component (c)) comprise fatty acid methyl esters derived from seed oils of sunflower, soybean, rapeseed, cotton, linseed, oil palm or coconut (including mixtures thereof). Of particular note is a composition of the invention wherein component (c) comprises fatty acid methyl esters derived from seed oils of soybean, rapeseed or coconut (including mixtures thereof). Methylated soybean, rapeseed and coconut oils have cloud points near 0° C. Also of particular note is a composition of the invention wherein the one or more fatty acid esters of alkanols (i.e. component (c)) comprise fatty acid methyl esters derived from soybean oil (also known as methylated soybean oil or methyl soyate). One example of fatty acid methyl esters derived from soybean oil is AGNIQUE ME 18 SD (including the product made in the U.S.A. and marketed as AGNIQUE ME 18 SD-U) from BASF. Also of note is component (c) comprising methylated coconut oil, particularly in combination with methylated soybean oil to provide a wide range of fatty acid esters. Methylated coconut oil has a high degree of saturation (absence of carbon-carbon double bonds) and thus is more resistant to oxidation than many other methylated seed oils.

Fatty acid esters of alkanols and methods for their preparation are well known in the art. For example, "biodiesel" typically comprises fatty acid esters of ethanol or more commonly methanol. Two principal routes used to prepare fatty acid alkanol esters are transesterification starting with another fatty acid ester (often a naturally occurring ester with glycerol) and direct esterification starting with the fatty acid. A variety of methods are known for these routes. For example, direct esterification can be accomplished by contacting a fatty acid with an alkanol in the presence of a strong acid catalyst such as sulfuric acid. Transesterification can be accomplished by contacting a starting fatty acid ester (e.g., a triglyceride) with the alcohol in the presence of a strong acid catalyst such as sulfuric acid but more commonly a strong base such as sodium hydroxide.

Alkylated seed oils are the transesterification products of seed oils with an alkanol. For example methylated soybean oil, also known as methyl soyate, comprises methyl esters produced by the transesterification of soybean oil with methanol. Methyl soyate thus comprises methyl esters of fatty acids in the approximate molar ratio that the fatty acids occur esterified with glycerol in soybean seed oil. Alkylated seed oils such as methyl soyate can be fractionally distilled to modify the proportion of methyl fatty acid esters, but such modification of the proportion of methyl fatty acid esters typically provides no advantage for the composition of the present invention. However, distillation can be beneficial for providing a purified alkylated seed oil. AGNIQUE ME 18 SD (including the U.S.A.-made product AGNIQUE ME 18 SD-U) consists of distilled methylated soybean oil.

In the present composition, the liquid carrier comprises as component (c) one or more fatty acid esters of $C_1$-$C_4$ alkanols, typically as the main (i.e. greater than 50% by weight) constituent of the liquid carrier. Therefore component (c) can be considered to form the liquid carrier. Components of the composition having good solubility in alkanol fatty acid esters are typically mostly or completely dissolved in the liquid carrier. In contrast, components of the composition, such as components (a) and (b), having low solubility in alkanol fatty acid esters are typically dispersed as solid particles in the liquid carrier. Because fatty acid esters of $C_1$-$C_4$ alkanols have relatively low viscosity compared to vegetable oils, they provide a liquid carrier having low viscosity, which improves the pourability of the present composition, thus facilitating dispensing. Besides providing the liquid carrier for the components of the invention either dissolved or dispersed, the fatty acid esters of $C_1$-$C_4$ alkanols also can help provide rainfastness after the composition has been diluted with water, sprayed on foliage of vegetation to be controlled, and spray water evaporated.

The present composition includes as component (d) one or more surfactants having an emulsifier property (i.e. emulsifiers) in the amount of 5 to 25% of the composition by weight. More typically, component (d) is at least 10%, but not more than 20% of the composition by weight.

The term "surfactant" is a shortened form of the term "surface-active agent". Surfactants have the useful tendency to migrate to interfaces (e.g., oil-water, air-water, water-solid) surfaces, resulting in a greater concentration at the interface than the surrounding bulk liquid phase. The propensity of surfactants to migrate to interfaces results from the combination of at least one hydrophobic (water-insoluble) group with at least one hydrophilic (water-soluble) group in the surfactant molecule. The hydrophobic group is also referred to as the lipophilic group or as the hydrophobe in many publications, because this group is soluble in liquids having low polarity, such as the fatty acid esters of $C_1$-$C_4$ alkanols of present component (c).

Although surfactants share the general tendency to migrate to interfaces, their properties can differ significantly, depending on the molecular structures of their hydrophobic and hydrophilic groups. Depending upon the structures of these surfactant molecule groups and the other components (e.g., solvents) present in the surfactant-containing medium, surfactants may have utility has emulsifying agents (i.e. emulsifiers), dispersing agents (i.e. dispersants), wetting agents, or foaming, anti-foaming or defoaming agents. Surfactants may have multiple functionalities, leading to multiple uses.

In the present composition, the liquid carrier is formed by one or more fatty acid esters of $C_1$-$C_4$ alkanols, which with low polarity, have very little solubility in water. Because the present herbicidal composition is typically first diluted with much greater amount of water in a spray system before application to the undesired vegetation to be controlled, for satisfactory performance the alkanol fatty acid ester component (c) in the present composition needs to form an oil-in-water emulsion when the composition is diluted with water. Component (d) is included to promote forming this emulsion. Therefore the one or more surfactants in component (d) must have an emulsifier property, specifically the ability to promote the formation of oil-in-water emulsions. The one or more surfactants in component (d) can also have, in addition, other surfactant utilities (e.g., wetting agent), but they must have significant ability to promote the formation of oil-in-water emulsions to be considered constituents of component (d).

Surfactants useful for forming oil-in-water emulsions are well known in the art. An extensive listing of commercially available surfactants, their chemical class and typical utility is given in *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964.

In addition to categorization of surfactants by functionality, functional classes are commonly further categorized according to the type of ion, or lack thereof, that the surfactant forms on addition to water, i.e. anionic, non-ionic or cationic. For the anionic and cationic subclasses, the ionic charge of significance in the classification is the charge on the hydrophilic moiety in the molecule, not the counterion. Typically in molecules of anionic or cationic surfactants, the charged hydrophilic group is the smallest portion of the molecule. In the molecules of non-ionic surfactants, the hydrophilic group is polar, but does not ionize.

The molecules of anionic surfactants have a hydrophilic group that ionizes to form an anion (negatively charged ion) when placed in an aqueous solution. Carboxylate, sulfate, sulfonate and phosphate are the most common hydrophilic groups in anionic surfactant molecules. Examples of anionic surfactants include: sodium alkylnaphthalene sulfonates, naphthalenesulfonate formaldehyde condensates, alkylbenzenesulfonates, lignin sulfonates, alkyl sulfates, alkyl ether sulfates, dialkyl sulfosuccinates, polycarboxylates, phosphate esters, ethoxylated tristyrylphenol phosphate salts and alkali salts of fatty acids.

The molecules of cationic surfactants have a hydrophilic group that ionizes to form a cation (positively charged ion) when placed in an aqueous solution. Examples of cationic surfactants include quaternary ammonium salts such as ethoxylated fatty amines, benzylalkylammonium salts, pyridinium salts and quaternary imidazolium compounds.

The molecules of non-ionic surfactants have a hydrophilic group that is polar but does not contain an ionizable functionality. Examples of non-ionic surfactants include: alkoxylated triglycerides; sorbitol and fatty acid esters, including their ethoxylates; ethoxylated sorbitan fatty acid esters; alkoxylated aliphatic alcohols; alkoxylated mono-, di- and tri-alkylphenols; alkoxylated mono-, di- and tri-styryl phenols; ethoxy, propoxy and butoxy block and random copolymers, such as polyoxyethylene-polyoxypropylene (EO/PO) block copolymers; and alkylpolyglycosides; wherein the term "alkoxylated" refers to the presence of one or more alkylene oxide-derived units, e.g., one or more units such as oxyethylene units (—$OCH_2CH_2$—) derived from ethylene oxide, oxypropylene units (—$OCH(CH_3)CH_2$—) derived from propylene oxide, and oxybutylene units (—$OCH(CH_2CH_3)CH_2$—) derived from butylene oxide. The prefix "poly" is often included in the name of a surfactant subclass or specific surfactant itself, if on average, more than one oxyalkylene unit is present in each surfactant molecule, e.g., "polyoxyethylene" and "polyoxypropylene". Alternatively, a "POE" or "POP" number may be included in the name to indicate the number of polyoxyethylene or polyoxypropylene, respectively, units present on average in each molecule.

To form present component (d), both anionic and non-ionic surfactants, particularly mixtures of these two general classes, are found to be useful. Anionic surfactants and non-ionic surfactants can be selected based on their reported utility as oil-in-water emulsifiers. Non-ionic surfactants can be also selected based on their HLB (Hydrophile-Lipophile Balance) values.

The HLB system or index is well known to those skilled in the art. HLB values for non-ionic surfactants are readily available in textbooks (e.g., A. W. Adamson, Physical Chemistry of Surfaces, John Wiley and Sons, 1982), and product technical data sheets and bulletins from commercial suppliers.

The HLB system is loosely based on the type and size of a surfactant molecule's hydrophobic and hydrophilic moieties and qualitatively trends with the polarity of the surfactant molecule. The HLB scale ranges from about 1 to 40, with the most commonly used non-ionic surfactants having values between 1 and 20. Increasing HLB indicates increasing hydrophilicity, e.g., increasing potential for the surfactant molecules present in an oilwater interface to increase the statistical distribution of their position and orientation in the interface so that the surfactant molecule on average penetrates deeper into the water phase as the HLB increases. Ranges of HLB values and the corresponding behaviors of non-ionic surfactants typically observed on addition to water are: less than 7, poor or no dispersibility in water (hydrophobic); greater than 12, clear solutions in water (hydrophilic); between 7 and 12, showing a progressive transition with increasing HLB, going from coarse, milky white, relatively unstable dispersions in water to cloudy and, in some cases, translucent emulsions, having improved stability against coalescence and phase separation.

As constituents useful in present component (d) having an emulsifier property, non-ionic surfactants typically have HLB values in the range of about 8 to about 12. However, blends of non-ionic surfactants having HLB values in the range of about 8 to about 12 are also useful even if the HLB values of the individual surfactants are outside of this range.

The HLB value of non-ionic surfactant blends can be determined by calculating the mass-weighted average HLB of the mixture. Thus the HLB value of the mixture equals the sum calculated by adding the product of the weight fraction of each constituent multiplied by the HLB of the constituent. For example, a 4:1 by weight mixture of TOXIMUL 2464F (HLB 9) with TOXIMUL 8240 (HLB 13) would have an HLB of 9.8, i.e. (0.8×9)+(0.2×13), where 0.8 is the fraction of 3464F in the mixture and 9 is its HLB value, and 0.2 is the fraction of 8240F in the mixture and 13 is its HLB value.

A wide range of anionic and non-ionic surfactants having utility for oil-in-water emulsions are suitable for forming component (d) of the present composition. Optimal selection of these surfactants for component (d) can be achieved through simple experimentation involving forming mixtures of the surfactants evaluated with one or more fatty acid esters of $C_1$-$C_4$ alkanols in various ratios, then adding the mixtures in an amount of about 1% to about 2% by weight of each to water, followed by thorough mixing and subsequent assessment of the quality and type of emulsion that forms.

Anionic surfactants of note as constituents of present component (d) are alkylbenzenesulfonates and alkylnaphthalenesulfonates. (These chemical classes of anionic surfactants are alternatively identified by names inserting one or more spaces, e.g., "alkylbenzene sulfonates", "alkyl benzene sulfonates", "alkylnaphthalene sulfonates", "alkyl naphthalene sulfonates".) Examples of alkylbenzenesulfonates and alkylnaphthalene-sulfonates include calcium dodecylbenzenesulfonate (e.g., RHODACAL 70/B (Rhodia), PHENYLSULFONAT CA100 (Clariant)), isopropylammonium dodecylbenzenesulfonate (e.g., ATLOX 3300B (Croda)) and sodium diisopropyl naphthalenesulfonate (e.g., MORWET IP (DeSoto)).

Non-ionic surfactants of note as constituents of present component (d) are ethoxylated triglycerides, ethoxylated tri-styryl phenols, ethoxylated aliphatic alcohols, ethoxylated sorbitan mono- and tri-esters, ethoxylated sorbitol hexa-esters and polyoxyethylene-polyoxypropylene block copolymers. Commercially available ethoxylated triglycerides are typically produced by ethoxylating seed oils (e.g., from soybean, rapeseed or castor bean) with from 10 to 40 moles of ethylene oxide. Examples of ethoxylated triglycerides include ethoxylated castor oil (e.g., TOXIMUL 8240F and TOXIMUL 8242F (Stepan), EMULSOGEN EL 360 (Clariant)) and ethoxylated soybean oil (e.g., AGNIQUE SBO-10 and AGNIQUE SBO-30 (Cognis, now BASF)). Commercially available ethoxylated tri-styryl phenols particularly useful for present component (d) typically contain an average of about 10 to about 20 oxyethylene units. Examples of ethoxylated tri-styryl phenol products include EMULSOGEN TS 160 (Clariant) and SOPROPHOR BSU (Rhodia). Ethoxylated aliphatic alcohols (also known as fatty alcohol ethoxylates) are generally prepared from $C_8$-$C_{22}$ alkanols or alkenols, which may be branched but are more typically linear. Commercially available ethoxylated aliphatic alcohols particularly useful for present component (d) typically contain an average of about 3 to about 15 oxyethylene units. Examples of ethoxylated aliphatic alcohol products include SYNPERONIC All (Uniqema) and GENAPOL LA 070 (Clariant). Examples of ethoxylated sorbitan mono- and tri-esters include polyoxyethylene (4) sorbitan monolaurate (e.g., TWEEN 21 (Croda)) and polyoxyethylene (20) sorbitan tristearate (TWEEN 65 (Croda)). Examples of ethoxylated sorbitol hexa-esters include polyoxyethylene (40) sorbitol hexaoleate (e.g., ATLAS G-1086 (Croda)). Examples of polyoxyethylene-polyoxypropylene block copolymers include PLURONIC F108 (BASF), and ATLOX 4912, ATLAS G-5000 (Croda) and SYNPERONIC PE Series copolymers (Croda). Of note also are combinations of surfactants in these non-ionic surfactant classes, particularly to provide non-ionic surfactant blends with an HLB value of 8 to 12.

Combinations of surfactants (i.e. surfactant blends) have been discovered to work well for component (d) to emulsify the one or more fatty acid esters of $C_1$-$C_4$ alkanols of component (c) on dilution with water. Of particular note is present component (d) consisting of a mixture of surfactant constituents, each having an emulsifier property, wherein at least one surfactant constituent is selected from anionic surfactants, such as a calcium or magnesium salt of an alkylbenzenesulfonate, and at least one surfactant constituent is selected from non-ionic surfactants, such as a polyoxyethylene-polyoxypropylene block copolymer. Other non-ionic surfactants, also typically comprising ethoxylation, are useful in these combinations as well. In the combination of an anionic surfactant with a nonionic surfactant, the anionic surfactant is often the primary emulsifier, but the nonionic surfactant further assists the emulsification process and provides emulsion stability. Besides having an emulsifier property, the nonionic surfactant can often act as a defoamer to counteract the foaming property of the anionic surfactant and can also act as a wetting agent to further improve biological performance. Certain anionic and non-ionic surfactants can also help disperse particulates. Combinations of anionic and non-ionic surfactants are commercially available, thus obviating need for the formulator to mix separate constituents. Examples of such non-ionic/ionic surfactant blends include ATPLUS 300F (Croda) and Emulsogen ITL (Clariant).

The present composition optionally further includes (e) up to 40% of one or more biologically active agents other than metsulfuron-methyl and thifensulfuron-methyl. When component (e) is present, typically it is at least 0.1% and more typically at least 5%, 10%, 15%, 20% or 35% of the composition by weight. Also, when component (e) is present, typically it is not more than 35%, more typically not more than 30%, of the composition by weight.

The other biologically active agents of component (e) may include herbicides other than metsulfuron-methyl and thifensulfuron-methyl, and may also include herbicide safeners, plant growth regulators, insecticides, insect antifeedants, miticides, nematocides, bactericides and fungicides, including both chemical and biological agents. Most commonly, the other active biologically agents of component (e) are herbicides or herbicide safeners. Examples of herbicides include acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil and its esters such as bromoxynil heptanoate and bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, cyclopyrimorate, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr and its esters such as fluroxypyr-meptyl, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, molinate, monolinuron, napropanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxy amid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thiobencarb, tiafenacil, tiocarbazil, tolpyralate, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifludimoxazin, trifluralin, triflusulfuron-methyl, tritosulfuron, vemolate, 3-(2-chloro-3,6-difluorophenyl)-4-hydroxy-1-methyl-1-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)-methoxy]methyl]-4,5-dihydro-5-methyl-3-(3-methyl-2-thienyl)isoxazole, 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione, 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methyl-sulfonyl)-N-(1- methyl-1H-tetrazol-5-yl)-4-(trifluoromethyl)benzamide and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub. Examples of herbicide safeners include allidochlor, benoxacor, cloquintocet-mexyl, cyometrinil, cyprosulfonamide, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(amino-carbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2-methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate.

Of note as biologically active agents in component (e) of the present composition are biologically active chemical compounds, such as herbicides or herbicide safeners, that are liquids or solids having a melting point less than 100° C., particularly less than 90° C., 80° C. or 70° C., and most particularly not greater than 60° C., because liquid and low-melting solid biologically active compounds are difficult to formulate in solid compositions. In the present composition, such liquids and low-melting solids typically dissolve in the liquid carrier formed by component (c). Also of note in component (e) of the present composition are biologically active agents typically applied at application rates of at least 100 g/ha when applied alone, because their higher application rates necessitate their concentrations to be correspondingly much greater than the concentration of metsulfuron-methyl in the present composition, which then requires the concentration of metsulfuron-methyl to be not more than 1% by weight, resulting in excessive decomposition on storage in the absence of a stabilizer, such as thifensulfuron-methyl as now discovered.

Of particular note in this regard as possible constituents of component (e) are fluroxypyr esters and bromoxynil esters.

When one or more fluroxypyr esters are present in the composition, the fluroxypyr ester constituent is typically at least 5%, more typically at least 15% and not more than 40%, more typically not more than 25% by weight of the composition. Examples of fluroxypyr esters include fluroxypyr-2-butoxy-1-methyethyl (2-butoxy-1-methylethyl [(4-amino-3,5-dichloro-6-fluoro-2-pyridinyl)oxy]acetate), which is a liquid at room temperature, and fluroxypyrmeptyl (1-methylheptyl [(4-amino-3,5-dichloro-6-fluoro-2-pyridinyl)oxy]-acetate), which melts at 58.2-60° C.

When one or more bromoxynil esters are present in the composition, the bromoxynil ester constituent is typically at least 5%, more typically at least 25% and not more than 40%, more typically not more than 35% of the composition by weight. Typically the bromoxynil esters are $C_6$-$C_{10}$ alkanoate esters of bromoxynil. Examples of bromoxynil esters include bromoxynil heptanoate (2,6-dibromo-4-cyanophenyl heptanoate) and bromoxynil octanoate (2,6-dibromo-4-cyanophenyl octanoate), which melts at 45-46° C.

The present composition optionally further includes (f) up to 63% of one or more additional formulating ingredients, alternatively described as auxiliaries, not otherwise corresponding to components (a) through (e). Examples of additional formulating ingredients are surfactants not having a significant emulsifier property, thickening agents, liquid and solid diluents, dyes, drying agents and the like. These ingredients are known to one skilled in the art and can be found described, for example, in *McCutcheon's 2001, Volume 2: Functional Materials* published by MC Publishing Company.

When component (f) is present, typically it is at least 0.1%, and more typically at least 1%, 2% or 3% of the composition by weight. Also, when component (f) is present, more typically it is not more than 50%, 40%, 30%, 20%, 15% or 10% of the composition by weight to accommodate substantially greater than minimal amounts of components (a) through (e).

Of note as examples of possible additional formulating ingredients are surfactants not having a significant emulsifier property, as well as thickening agents. Of note is a composition of the invention wherein component (f) comprises at least one constituent selected from (1) from surfactants not having a significant emulsifier property, particularly surfactants having a dispersant property, and (2) thickening agents. Of particular note is a composition of the invention wherein component (f) comprises at least one constituent selected from (1) surfactants not having a significant emulsifier property, particularly surfactants having a dispersant property, and also at least one constituent selected from (2) thickening agents.

When solid particulates, such as particles of present components (a) and (b), are in suspension, whether oil-based (e.g., suspended in the one or more fatty acid esters of $C_1$-$C_4$ alkanols of present component (c)) or aqueous-based (e.g., suspended in water after dilution of the present composition with water), their kinetic energy and trajectory can force them close enough together such that their mutual attractive forces overcome their mutual repulsive forces. In some instances, this can result in a flocculation or coagulation of the particles, i.e. they can loosely stick together ("weak flocculation") or irreversibly agglomerate ("coagulation"). Dispersing agents, also called dispersants, are surfactants that can influence (e.g., reduce) the degree to which both organic and inorganic particulate solids interact and thereby stabilize their suspension.

Dispersing agents are generally either anionic or nonionic surfactants and are often polymeric. Anionic dispersing agents include alkylnaphthalene sulfonates and their formaldehyde condensates (e.g., MORWET D425), polyalkylaryl sulfonates (e.g., SUPRAGIL MNS90), polymerized fatty acids (e.g., ATLOX LP-1 (12-hydroxyoctadecanoic acid homopolymer, octadecanoate), ricinoleic acid homopolymer), lignin sulfonates (e.g., ammonium lignosulfonate or sodium lignosulfonate), polyphenol sulfonates and the salts of polyacrylic acids. Non-ionic dispersing agents include phosphate esters of tristyrylphenol ethoxylates (e.g., SOPROPHOR 3D33, ethoxylated triglycerides, ethoxylated aliphatic alcohols, polyoxyethylenepolyoxypropylene (EO/PO) block copolymers (e.g., PLURONIC F108, ATLOX 4912, ATLAS G-5000, SYNPERONIC PE Series copolymers) and ethylene oxidepropylene oxide based acrylic acid graft copolymers such as methyl methacrylate graft copolymers (e.g., ATLOX 4913).

As already mentioned, surfactants generally modify the surface tension of a liquid, and depending on the nature of the hydrophilic and lipophilic groups in a surfactant molecule, surfactants can be useful as emulsifying agents (i.e. emulsifiers), dispersing agents (i.e. dispersants), wetting agents or antifoaming agents (i.e. defoamers). Furthermore, depending upon molecular structure, a particular surfactant may have more than one useful surfactant property. For example, a surfactant may be useful as a both an emulsifier and a dispersant.

In the context of the present disclosure and claims, a surfactant having an emulsifier property, i.e., an emulsifier, is a surfactant known to be useful for forming oil-in-water emulsions. Furthermore, a surfactant having an emulsifier property is considered to be a constituent of component (d) irrespective of whether it may also be useful as a dispersing agent, wetting agent or defoamer.

Inclusion in present component (f) of one or more surfactants having a dispersant property but not an emulsifier property is optional, particularly if one or more surfactants of component (d) have a dispersant property in addition to an emulsifier property. Examples of surfactants having both emulsifier properties and dispersant properties include alkylnaphthalene sulfonates, ethoxylated triglycerides, ethoxylated aliphatic alcohols and polyoxyethylene-polyoxypropylene block copolymers. However, including a surfactant optimized for a dispersant property while having no significant emulsifier property can achieve optimum results for preventing flocculation and coagulation of components (a) and (b) in the liquid carrier formed by component (c) and/or the aqueous mixture for spraying formed after dilution of the present composition in water. When such a dispersant is present in the composition, it is typically at least 0.1%, more typically at least 2% of the composition by weight. Also when a dispersant is present in the composition, it is typically not more than 5% of the composition by weight. Polymerized fatty acids such as ATLOX LP-1 have been found to work particularly well in such amounts as dispersants in the present composition.

Component (f) may also comprise surfactants having additional useful properties other than an emulsifier property, such as wetting agents and anti-foam agents.

Although optional, particularly if the present composition is used soon after preparation, typically one or more thickening agents (also known as thickeners, rheology modifiers or suspending agents) are included as part of component (f) to prevent undesirable phase separation and/or sedimentation of solid particles (e.g., of components (a) and (b)) that can occur in unstructured suspension concentrates during storage. Thickening agents increase the viscosity of the continuous liquid medium in which solid particles (e.g., of components (a) and (b)) are suspended and thus reduce their propensity to settle and form a separated, compact sediment during storage. Also, a thickening agent may improve the efficiency of a wet milling process used to prepare the present composition. When a thickening agent is present is the composition, it is typically at least 0.1%, more typically at least 0.5%, of the composition by weight. Also when a thickening agent is present, typically it is not more than 5%, and more typically not more than 4%, 3% or 2% of the composition by weight.

Thickening agents are well known in the art of formulations. For the present composition having a liquid carrier comprising one or more fatty acid esters of $C_1$-$C_4$ alkanols, thickening agents are generally selected from silicas and silicates, which may be naturally occurring, artificially produced, or organically modified.

Silicas include synthetic precipitated or fumed silicas, which may be chemically (including organically) modified, for example with dimethyldichlorosilane, to increase hydrophobicity. Such silicas are commercially available under a variety of trade names (e.g., SIPERNAT or AEROSIL (Evonick), CAB-O-SIL (Cabot)). An example of a hydrophobic fumed silica treated with dimethyldichlorosilane is AEROSIL R974 (Evonik).

Silicates include phyllosilicate minerals having particles of less than 2 μm size present in naturally occurring clays, such as kaolinite and smectites (e.g., smectite, hectorite, attapulgite, montmorillonite), and their combinations such as bentonites. Clays comprising minerals of the smectite group generally can be organically chemically modified by cation exchange of metal ions with organic salts such as quaternary ammonium salts to increase hydrophobicity. Natural and modified clays are commercially available under a variety of trade names (e.g., BENTONE (Elementis), BARDEN clay (Kentucky Tennessee Clay Co.), ATTAGEL (BASF), MIN-U-GEL (Active Minerals)). Organic chemical modification of clays through surface treatment with quaternary ammonium salts renders them more effective for rheology modification (particularly thickening under low-shear conditions) in non-aqueous systems, such as the liquid phase of the present composition formed from one or more fatty acid esters of $C_1$-$C_4$ alkanols (i.e. component (c)). Examples of organically modified clays include GARAMITE 1958 and CLAYTONE 40 (Southern Clay Products) and BENTONE 34 and BENTONE 1000 (Elementis). Organically modified clays work particularly well as thickening agents in the present composition. Of note is the composition of the present invention comprising by weight 0.5 to 5% of one or more organically modified clays.

As already noted, the present composition has a single liquid phase wherein the liquid carrier comprises as component (c) one or more fatty acid esters of $C_1$-$C_4$ alkanols. The single liquid phase requirement precludes the presence of liquid phases in addition to the continuous liquid phase formed by component (c). Therefore while solid particles, such as of components (a) and (b) can be suspended as a dispersion in the liquid phase formed by component (c), liquid droplets of other substances cannot be present, such as in an emulsion, in the liquid phase. Therefore any water that is present in the composition must be dissolved in the liquid phase formed by component (c) or absorbed into particles of solid substances suspended in the liquid phase, but not present as an emulsion. This inherently greatly limits the amount of water that can be present.

Even for technical grade fatty acid esters of $C_1$-$C_4$ alkanols containing polar impurities, e.g., biodiesel, the solubility of water at room temperature is typically less than 2% by weight. Although other ingredients in the present composition may accommodate additional water while maintaining a single liquid phase, generally the present composition does not contain more than 10% water by weight, and typically not more than 5% water by weight. Lesser amounts of water may be advantageous for better stability of the ingredients, so preferably the present composition does not contain more than 3%, 2% or even 1% water by weight.

The present composition can be easily prepared by combining the component ingredients and reducing the particle size of insoluble components (e.g., components (a) and (b)) in the liquid carrier formed by component (c). As is well known in the art, particle size reduction of insoluble components in an oil dispersion can be beneficial for providing stable homogeneous suspensions, as well as maximizing bioefficacy of the composition. Generally to produce stable suspensions, the size of particles in the suspension should be not greater than 50 μm, preferably not greater than 10 μm, and most preferably not greater than 5 μm. Typically the size of the particles is at least 1 μm.

A variety of methods for reducing particle size of insoluble components in oil dispersions are known in the art and suitable for preparing the present composition. These include ball-milling, bead-milling, sand-milling, colloid-milling and air-milling combined with high-speed blending. Ball-, bead- and sand-mills are media mills that achieve size reduction of particles by vigorous agitation with grinding media (e.g., balls or beads made of glass or ceramic, or sand). In ball-mills, typically the container rotates, while in bead- or sand-mills, grinding is achieved by an impeller in the grinding media. In horizontal bead-mills, agitation is by the action of an internal agitator rapidly rotating along the axis of the milling chamber. Colloid mills achieve size reduction of particles by passing the material to be ground through a narrow gap of a rapidly rotating rotor-stator assembly. Ball-milling, bead-milling, sand-milling and colloid-milling generally involve wet-milling (i.e. the liquid carrier is present). Air-milling is suitable for dry powders (e.g., present components (a) and (b)), which would then be combined with liquid components (e.g., present component (c)) and high-speed blended using high-speed impellers or dispersators (i.e. rotor-stator).

For sake of convenience, the present components can be combined before milling. Thus in this process for preparing the composition of the invention, components (a) and (b) are milled together in a liquid carrier comprising components (c) and (d), and any other components (e.g., component (e) and (f) are present either dissolved or as solid particulates in the milling mixture. Bead-milling has been found to work very well for preparing the present composition. The Examples of the present disclosure use an Eiger Minimill, which is a laboratory-scale horizontal bead mill found capable of providing a particle size distribution (analyzed by Mastersizer 2000, Fraunhofer presentation mode, dilution with 2-propanol) having D10, D50 and D90 percentiles of 1.0-2.0 μm, 3.0-6.0 μm, and 9.0-15.0 μm, respectively. (This mill is now marketed as an EMI Mini Series Mill by Engineered Mills, Inc., Grayslake, Ill.) Similar particle size reduction can also be achieved on a larger scale by utilizing equipment such as, but not limited to, Dyno-mill horizontal bead mills (Willy A Bachofen AG) and related types of low energy mills or high energy mills, for instance those available from Netzsch (Netzsch-Feinmahltechnik GmbH) or Buhler (Buhler Group).

Although the present composition can be applied directly to undesired vegetation to be controlled or to the growing medium thereof, generally the composition is first diluted with water in a volume ratio of 1:50 to 1:1000, more typically 1:100 to 1:600 of present composition to water. Dilution of the present composition with water using agitation provides a spray mixture comprising an aqueous dispersion of particles of components (a) and (b), and an emulsion of component (c) in the water. The spray mixture is then applied to undesired vegetation (e.g., foliage) or to the growing medium (e.g., soil) of the undesired vegetation. For optimal herbicidal efficacy, most typically the spray mixture is applied to the foliage of the undesired vegetation. One skilled in the art can readily determine the optimal amount of spray mixture to apply based on the active herbicides and their concentrations in the composition, the dilution ratio of the composition in water, the nature and growth stage of the undesired vegetation, and environmental conditions. Often the spray mixture is applied in an amount of 50 to 1000 L/ha, more typically 100 to 600 L/ha. Without further elaboration, it is believed that one skilled in the art using the preceding description can utilize the present invention to its fullest extent. The following non-limiting Examples are illustrative of the invention.

FORMULATION EXAMPLES

The following examples describe preparation of compositions of the present invention as well as comparative compositions omitting the thifensulfuron-methyl stabilizer (i.e. component (b)). Technical grade metsulfuron-methyl, thifensulfuron-methyl and fluroxypyr-meptyl were used to prepare the example compositions. The inert formulating ingredients are identified in Table 1.

TABLE 1

Identity of Inert Formulating Ingredients Used in the Examples

| Ingredient | Manufacturer | CAS Registry No. | Chemical Composition | Function |
|---|---|---|---|---|
| AGNIQUE ME 18 SD-U | BASF | 68919-53-9 | Distilled methylated soybean oil ($C_{16}$-$C_{18}$ fatty acid methyl ester) | Liquid carrier |
| ATPLUS 300F | Croda | 73468-21-0 | Non-ionic/ionic surfactant blend | Emulsifier |
| ATLOX LP-1 | Croda | 58128-22-6 | Polymerized fatty acids | Dispersant |
| BENTONE 1000 | Elementis | 887329-06-8 | Organically modified montmorillonite clay | Thickener |

In the present examples (i.e. Examples 1 and 2, and Comparative Examples 1 and 2) all the ingredients were thoroughly mixed and then subjected to milling in a Eiger Minimill (horizontal bead mill manufactured by Eiger Manufacturing Inc. (now Engineered Mills, Inc., Grayslake, Ill.); 50 mL chamber size with 80% loading of glass media, 0.8-1.0 mm in diameter) with the chamber cooled to about 6-10° C., using 3800 rpm agitator speed and recirculation mode for 20 minutes to provide the example formulated compositions.

Example 1

To a 400-mL plastic beaker equipped with an overhead stirrer was added a $C_{16}$-$C_{18}$ fatty acid methyl ester (AGNIQUE ME 18 SD-U, 155.04 g), a non-ionic/ionic emulsifier blend (ATPLUS 300F, 30.05 g), a polymeric fatty acid dispersant (ATLOX LP-1, 6.01 g), metsulfuron-methyl (1.03 g), thifensulfuron-methyl (6.01 g) and an organically modified clay (BENTONE 1000, 2.02 g). The stirred mixture was then milled using the Eiger Minimill to provide the finished formulated composition as a free-flowing suspension.

Comparative Example 1

To a 400-mL plastic beaker equipped with an overhead stirrer was added a $C_{16}$-$C_{18}$ fatty acid methyl ester (AGNIQUE ME 18 SD-U, 161.03 g), a non-ionic/ionic emulsifier blend (ATPLUS 300F, 30.01 g), a polymeric fatty acid dispersant (ATLOX LP-1, 6.01 g), metsulfuron-methyl (1.03 g) and an organically modified clay (BENTONE 1000, 2.11 g). The stirred mixture was then milled using the Eiger Minimill to provide the finished formulated composition as a free-flowing suspension.

Example 2

To a 400-mL plastic beaker equipped with an overhead stirrer was added a $C_{16}$-$C_{18}$ fatty acid methyl ester (AGNIQUE ME 18 SD-U, 114.98 g), a non-ionic/ionic emulsifier blend (ATPLUS 300F, 30.17 g), a polymeric fatty acid dispersant (ATLOX LP-1, 6.01 g), fluroxypyr-meptyl (40.28 g), metsulfuron-methyl (1.06 g), thifensulfuron-methyl (6.11 g) and an organically modified clay (BENTONE 1000, 2.08 g). The stirred mixture was then milled using the Eiger Minimill to provide the finished formulated composition as a free-flowing suspension.

Comparative Example 2

To a 400-mL plastic beaker equipped with an overhead stirrer was added a $C_{16}$-$C_{18}$ fatty acid methyl ester (AGNIQUE ME 18 SD-U, 121.16 g), a non-ionic/ionic emulsifier blend (ATPLUS 300F, 30.06 g), a polymeric fatty acid dispersant (ATLOX LP-1, 6.02 g), fluroxypyr-meptyl (40.03 g), metsulfuron-methyl (1.03 g) and an organically modified clay (BENTONE 1000, 2.11 g). The stirred mixture was then milled using the Eiger Minimill to provide the finished formulated composition as a free-flowing suspension.

The weight percentage amounts of the ingredients in the example formulated compositions are listed in Table 2.

TABLE 2

Ingredient Amounts Used in Example (Ex.) 1 and 2 and Comparative Example (C. Ex.) 1 and 2*

| Ingredient | Component | Ex. 1 | C. Ex. 1 | Ex. 2 | C. Ex. 2 |
|---|---|---|---|---|---|
| Metsulfuron-methyl | (a) | 0.5 | 0.5 | 0.5 | 0.5 |
| Thifensulfuron-methyl | (b) | 3.0 | 0 | 3.0 | 0 |
| AGNIQUE ME 18 SD-U | (c) | 77.5 | 80.5 | 57.5 | 60.5 |
| ATPLUS 300F | (d) | 15.0 | 15.0 | 15.0 | 15.0 |
| Fluroxypyr-meptyl | (e) | 0 | 0 | 20.0 | 20.0 |
| ATLOX LP-1 | (f) | 3.0 | 3.0 | 3.0 | 3.0 |
| BENTONE 1000 | (f) | 1.0 | 1.0 | 1.0 | 1.0 |

*Amounts are listed as wt/wt %.

When prepared, the compositions were analyzed by HPLC for metsulfuron-methyl and thifensulfuron-methyl content. The stability of metsulfuron-methyl and thifensulfuron-methyl in the compositions prepared was then determined by aging samples in ovens at 40° C. for 4 and 8 weeks. Storage at 40° C. at 8 weeks simulates two-year storage at ambient temperature. Control samples were stored in a freezer at −6° C. Assays of the control samples at the various time points were comparable to the initial, as-made assays. At the end of the allotted times, samples were removed from the ovens and analyzed by HPLC for metsulfuron-methyl or thifensulfuron-methyl content. The relative chemical stability was calculated by dividing the assay of the oven-aged sample by that of the control sample analyzed on the same day. Chemical stability results are listed in Table 3.

TABLE 3

Chemical Stability of Metsulfuron-methyl and Thifensulfuron-methyl (% Relative Stability) During Aging of Compositions of Example (Ex.) 1 and 2 and Comparative Example (C. Ex.) 1 and 2 at 40° C.

| Time period | % Relative Stability ||||||||
|---|---|---|---|---|---|---|---|---|
| | Metsulfuron-methyl |||| Thifensulfuron-methyl ||||
| | Ex. 1 | C. Ex. 1 | Ex. 2 | C. Ex. 2 | Ex. 1 | C. Ex. 1 | Ex. 2 | C. Ex. 2 |
| 4 weeks | 92.3 | 75.5 | 89.1 | 75.0 | 98.5 | — | 99.2 | — |
| 8 weeks | 88.7 | 50.0 | 80.4 | 47.4 | 98.9 | — | 97.0 | — |

As can be seen from the stability results for Comparative Examples 1 and 2 in Table 3, in the absence of thifensulfuron-methyl (component (b) of the present invention), one-quarter of the metsulfuron-methyl was degraded at 4 weeks and one-half of the metsulfuron-methyl was degraded at 8 weeks in this test. However as shown for Examples 1 and 2, adding just 3% of thifensulfuron-methyl as component (b) to the 0.5% of metsulfuron-methyl by weight of the composition surprisingly slowed the decomposition of metsulfuron-methyl to a remarkable extent, such that after 8 weeks more than 80% of the metsulfuron-methyl remained. Besides functioning as a stabilizer of the metsulfuron-methyl, the thifensulfuron-methyl component itself showed excellent stability.

What is claimed is:

1. A single liquid-phase herbicide composition comprising by weight of the composition:
   (a) from 0.1 to 1% of metsulfuron-methyl;
   (b) from 1 to not more than 10% of thifensulfuron-methyl;
   (c) from 30 to 93% of one or more fatty acid esters of $C_1$-$C_4$ alkanols; and
   (d) from 5 to 25% of one or more surfactants having an emulsifier property selected from the group consisting of alkylbenzenesulfonates, alkylnaphthalenesulfonates, ethoxylated triglycerides, ethoxylated tri-styryl phenols, ethoxylated aliphatic alcohols, ethoxylated sorbitan mono- and tri-esters, ethoxylated sorbitol hexaesters and polyoxyethylene-polyoxypropylene block copolymers, and mixtures thereof; and
   (e) at least 5% of one or more fluroxypyr esters.

2. The composition of claim 1 wherein component (c) comprises one or more methylated vegetable oils.

3. The composition of claim 2 wherein component (d) comprises at least one surfactant selected from anionic surfactants and at least one surfactant selected from nonionic surfactants.

4. The composition of claim 2 further comprising (f) up to 63% of one or more additional formulating agents.

5. The composition of claim 2 wherein component (c) comprises one or more methylated seed oils or soybean, rapeseed or coconut.

6. The composition of claim 5 wherein component (c) comprises methylated soybean oil.

7. The composition of claim 1 wherein component (d) comprises at least one surfactant selected from anionic surfactants and at least one surfactant selected from nonionic surfactants.

8. The composition of claim 1 further comprising (f) up to 63% of one or more additional formulating agents.

9. The composition of claim 8 wherein component (f) comprises one or more organically modified clays.

10. The composition of claim 8 wherein component (f) comprises one or more polymerized fatty acids.

11. The composition of claim 10 wherein component (f) comprises one or more organically modified clays.

12. The composition of claim 1 wherein component (c) in its isolated form has a cloud point less than 15° C.

13. A process for preparing the composition of claim 1, the process comprising milling components (a), (b) and (e) together in a liquid carrier comprising components (c) and (d).

* * * * *